United States Patent [19]
Schumann

[11] 4,014,094
[45] Mar. 29, 1977

[54] DENTAL HINGE STRUCTURE

[76] Inventor: Allan H. Schumann, 3405 N. Countryside Drive, McHenry, Ill. 60050

[22] Filed: July 24, 1975

[21] Appl. No.: 598,792

[52] U.S. Cl. .................................................. 32/5
[51] Int. Cl.² ........................................ A61C 13/22
[58] Field of Search ................................... 32/5, 6

[56] References Cited
UNITED STATES PATENTS 2,797,482  7/1957  Zahn .................................. 32/5

FOREIGN PATENTS OR APPLICATIONS 533,113  8/1954  Italy .................................. 32/5

Primary Examiner—Robert Peshock
Attorney, Agent, or Firm—Richard G. Kinney

[57] ABSTRACT

A hinge bar and product assembly for use in manufacture of partial dentures including a hinge bar having a cylindrical end surface thereon adapted to be received internal of a mating support member attached to supporting natural teeth. The cylindrical end surface of the hinge bar closely fitting the internal mating surfaces of the support therefor and having at the top portion thereof a stop surface to limit movement of the bar with respect to the support and having at the other end thereof notches which are adapted to receive an attaching member to be cast therearound, providing an extremely compact hinge assembly providing exceptional strength in preventing horizontal or lateral movement of the hinge bar thereof with respect to the support and presenting no pockets and/or recesses in which food or moisture can collect.

9 Claims, 8 Drawing Figures

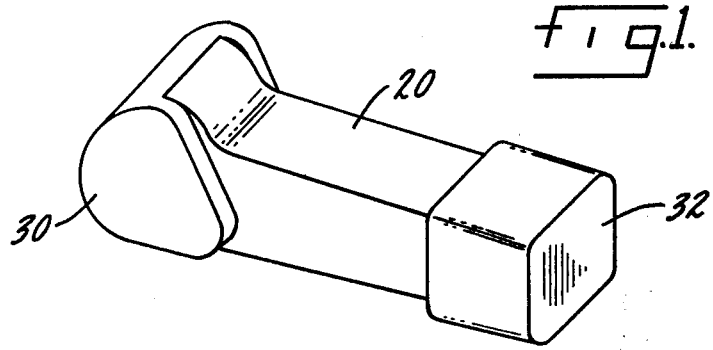
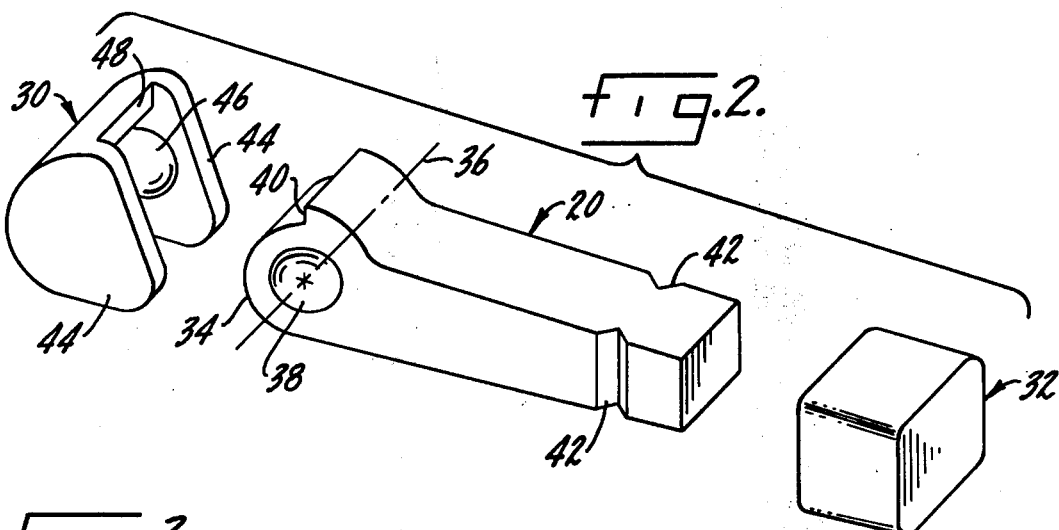
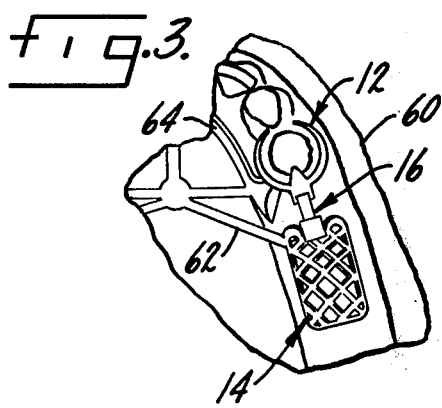
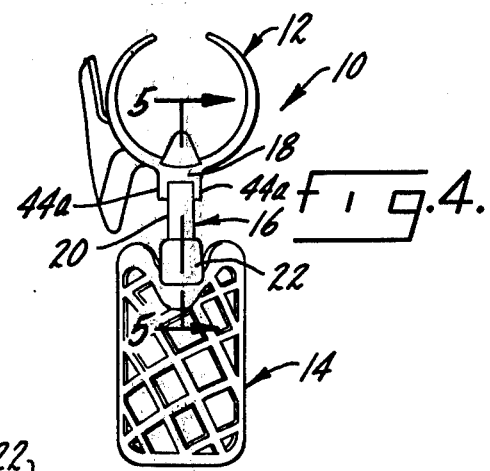
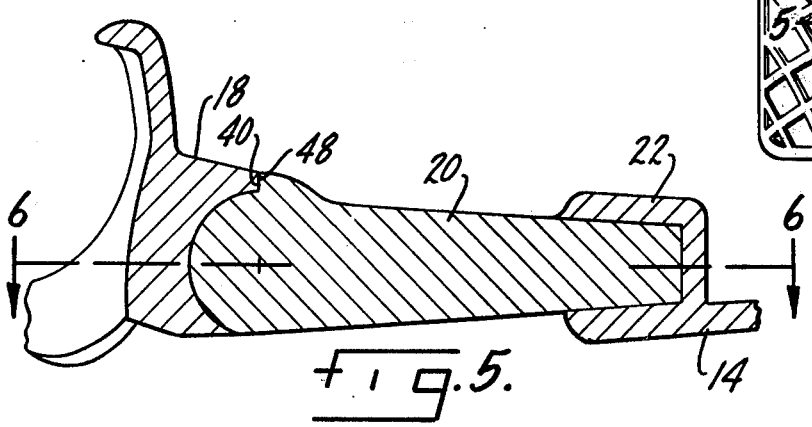

DENTAL HINGE STRUCTURE

SUMMARY OF THE INVENTION

It has been found, in prior art devices of the type including hinge means for attaching support members for artificial teeth of partial dentures to supporting natural teeth, that expensive and complicated hinge assemblies are normally used as for example as shown in U.S. Pat. Nos. 3,025,500, 2,797,456, 2,798,294, 2,508,546 and others. These patents all show rather complicated structures which will present pockets or recesses in which food and moisture can collect. At the same time the structures are weak in resistance to horizontal or lateral movement of the hinge bar with respect to the support attached to the natural teeth rather than permitting solely the vertical movement desired.

The present invention solves the above problems by providing a hinge bar of the type having a cylindrical end surface which is received in a closely fitting support member attached to the supporting teeth. The support member having a generally three-sided hooded type shape surrounding the end of the hinge bar to seal out food and present no pockets for collection of food and moisture. At the same time the hooded structure surrounds three sides of the bar, resisting lateral or horizontal movement of the hinge bar with respect to its support with great strength. The present invention is of a very simple construction providing for a low cost hinge product assembly which a dentist or manufacturer of partial dentures can purchase to provide the hinged section between the clasp section to be attached to the natural teeth and the saddle member to support artificial teeth. Other unique advantages and functions of the present invention will be apparent from the following description.

BRIEF DESCRIPTION OF THE DRAWINGS

FIG. 1 is a perspective view of a hinged product assembly of the present invention;

FIG. 2 is an exploded view of the assembly of FIG. 1;

FIG. 3 is a plan view of a casting model ready for use in manufacturing a dental device incorporating the hinge assembly of the present invention;

FIG. 4 is a detailed view of a part of the casting product of the structure of FIG. 3;

FIG. 5 is a sectional view taken along lines 5—5 of FIG. 4;

DESCRIPTION OF A PREFERRED EMBODIMENT OF THE INVENTION

Figure 6:
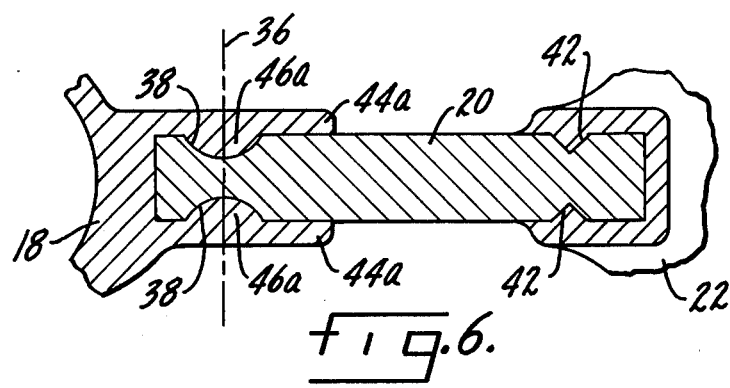
FIG. 6 is a sectional view taken along lines 6—6 of FIG. 5.

The present invention relates to an improved hinge product assembly and hinge bar for use in manufacture of partial dentures which are to be attached to supporting natural teeth. Referring first to FIG. 4, the overall assembly 10 in which the improved hinge is to be used is illustrated which is formed of cast metal and includes a clasp portion 12 adapted to be attached to natural teeth, a saddle portion 14 which will support the artificial teeth. The saddle portion 14 is adapted to fit over the gum of the wearer in the location of missing teeth. The hinge assembly 16 of the present invention connects clasp portion 12 to saddle portion 14. The support 12 includes a pivot part 18 which receives the hinge bar 20 of the present invention. The hinge bar 20 is permanently attached to the saddle 14. Saddle portion 14 includes a support part 22 connected to the hinge bar 20. The support part 18 surrounds the end of the hinge bar 20 in a hooded fashion to provide unique advantages to be later described.

Referring now to FIGS. 1 and 2, the hinge product assembly to be used in the manufacture of a partial denture as shown semi-finished in FIG. 4, is illustrated. This assembly comprises the hinge bar 20 to which is attached a temporary pivot member 30 at one end thereof and a temporary attachment member 32 attached to the opposite end of the bar 20. The bar 20 is generally rectangular in shape and includes a cylindrical end surface 34 thereon which has a center axis generally indicated at 36. Surrounding the axis 36 on either side of the bar 20 or bearing journal supports 38, which are generally in the shape of conical recesses adapted to receive bearing journals. The bar 20 pivots about the axis 36 when in use by pivoting around journals.

The cylindrical end surface 34 terminates on the upper side of the bar in a shoulder 40 which is parallel to axis 36 and surface 34 and forms a stop means limiting the pivot movement of bar 20. At the opposite end of the bar 20 a pair of vertical notches 42 are provided which serve as attachment means to attach pivot bar to attachment member 32. The temporary support member 30 is of a generally hooded shape which will surround the entire end portion of the bar 20 as illustrated in FIG. 1. The temporary pivot member 30 includes a pair of sides 44 which include interior thereof bearing journals 46 adapted to be received in journal supports 38 of the bar 20 and further includes a stop surface 48 adapted to engage with the surface of shoulder 40.

The hinge product assembly, as illustrated in FIG. 1, is constructed of diverse materials. The hinge bar 20 itself is of permanent metal and will remain as illustrated in FIG. 2 in the final product of the partial denture. However, the temporary pivot and attachment members are made of wax or plastic, which in the process for manufacturing the mold from which the metal appliance of FIG. 4 is to be constructed, will be removed or destroyed by heat. Thus the pivot and attachment members each serve as a pattern for the ultimate metal members. The pivot member pattern and the attachment member pattern are replaced by metal in the manufacturing process. This manufacturing process is known as the "lost wax process" and which is well known and described in U.S. Pat. No. 3,023,500 and others. The general principal thereof is to use wax or heat destructible products to provide a desired shape around which a hand investment plaster mold is formed in which can be cast the metal product shown in FIG. 4. By using a hinge bar of metal in finished form in the casting process, the necessary metal saddle portion 14 and clasp portion 12 are formed around hinge bar 20 and proper supporting and attaching relationships automatically established during the casting process.

Referring to FIG. 3, a wax form is illustrated to make a product of which FIG. 4 is only a part, there being usually an identical portion to FIG. 4 on the opposite side of the model of FIG. 3. The casing model 60 of FIG. 3 has formed thereon a clasp portion 12 and saddle portion 14, each made of wax. The hinge assembly 16 is shown in place in the casting model. Sprues 62 are also illustrated formed of wax which will provide passages in the plaster mold to supply metal through the mold to form the parts of the casting. Also illustrated is a lingual bar 64 used in products of this type for additional support for the partial denture which is also known in the prior art.

Referring again to FIG. 3, the process involves utilizing the hinge product assembly 16 of FIG. 1. The assembly 16 is placed on the casting model 60 in position between the clasp 12 and saddle 14 formed in wax and is secured in place by sufficient additional wax to surround and attach the end of pivot member or pattern 30 to clasp portion 12 and attachment member or pattern 32 to saddle portion 14. Thus, when the casting process is carried out the metal parts of FIG. 4 will be cast around the hinge bar 20 replacing the temporary pivot and attachment members 30 and 32 respectively.

Referring to FIGS. 5 and 6, it can be seen that in the casting process permanent metal bearing journals 46a are formed in each of the sides 44a of the pivot part 18 for clasp section 12 which provides a bearing structure for pivotal movement of the bar 20 about the axis 36. Such pivotal motion is necessary in dental appliances of this type because during the chewing process pressure applied on the teeth carried by the saddle portion 14 tends to place great stress on the supporting teeth to which clasp portion 12 is attached. By absorbing some of this stress by allowing the pivotal movement of the bar 20 in a clockwise direction, as illustrated in FIG. 5, the stress will be relieved and movement resulting from the natural resilience of the gum under saddle portion 14 is allowed. The stop surfaces 40 and 48 are normally in engagement, as shown in FIG. 5, which would be the normal position for parts of the dental appliance when in the users mouth. It can also be seen that during the casting process, as illustrated also in FIG. 6, the notches 42 of the bar 20 will receive complementary metal portions of the support part 22 attached to saddle portion 14, thus permanently attaching the hinge bar 20 to the saddle portion 14.

The unique advantage of the present invention is that the novel and unique hinge bar assembly 16 provides for easy manufacture of a hinge of the type illustrated in FIGS. 4, 5 and 6 which is of a construction such that the pivotal end of the hinge bar 20 is completely shrouded exposing no pockets or recesses which can collect food or moisture. Further, since the side portions 44a of the pivot part 18 of clasp portion 12 completely cover the end of the hinge bar 20 and include internal thereof journals for the pivotal movement of the bar 20, movement of the hinge bar with respect to the clasp portion in a lateral or horizontal direction is prevented. Only vertical movement or, i.e. clockwise or counterclockwise movement of the bar 20, referring to FIG. 5, is permitted. It will be apparent that an extremely strong pivotal connection is provided by the hooded structure including the pivot part 18. The closely fitting cooperation of the parts provides the strength of the hinge and eliminates pockets and recesses. In addition to providing additional strength an extremely compact pivotal connection is made as illustrated in FIGS. 3 and 4 allowing maximum space for attachment of teeth over the hinged joint shown in FIG. 4 which is required of the partial denture.

The parts illustrated in FIG. 1 and FIG. 2 comprising the hinge product assembly 16 may be shipped as illustrated in FIG. 1 as a unitary assembly which the manufacturer of the dental appliance of FIG. 4 can readily use to provide the hinge connection between the clasp portion 12 and the saddle portion 14 without the need to worry about the operational or dimensional problems with respect to the manufacture of a pivotal joint. The extremely simple nature of the pivotal connection between the hinge bar 20 and the pivot part 18 to which it is attached in final construction is advantageous in that a very simple structure is provided with minimal parts since the manufactured hooded pivotal part 18 includes the means to form both the supports for the pivotal movement, the stop means to limit pivotal movement and the strengthening and protecting side portions, all in a single part. As for example, when referring to prior art U.S. Pat. No. 3,025,500 it will be seen that the pieces needed to provide the hinge thereof include additional pieces 38 to form a bearing structure as illustrated in FIG. 9. In addition, the hinge product 20 itself of FIG. 9 of U.S. Pat. No. 3,025,500 is of a much more complex and difficult to manufacture nature. The disclosure of U.S. Pat. No. 3,023,500 is typical of the prior art patents which disclose complicated and expensive to manufacture joints which fail to offer the unique simpleness and low cost of the hinge assembly of the present invention.

Figure 7:
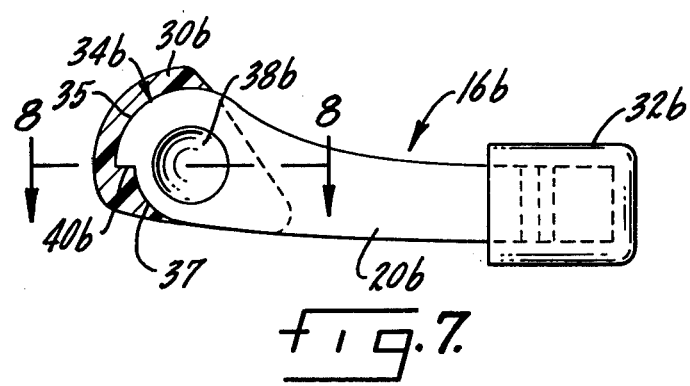
FIG. 7 is a view partially in section of a modified form of the hinge of the present invention.
Figure 8:
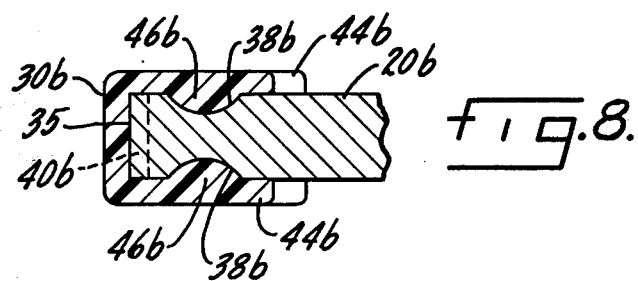
FIG. 8 is a sectional view taken along lines 8—8 of FIG. 7.

Referring to FIGS. 7 and 8, an alternative arrangement of hinge product assembly 16 of FIGS. 1 and 2 is illustrated. The main distinction of hinge product assembly 16b of FIG. 7 is that the stop shoulder 40b on bar 20b is on the end thereof along generally the mid-longitudinal axis of bar 20b. The cylindrical end surface 34b is formed in two spherical segments 35 and 37 separated by the shoulder 40b. Thus an even more protected and sealed pivotal joint is provided in that when the bar 20b pivots in a clockwise direction in use as viewed in FIG. 7, the opening between stop shoulder 40b and the surface in the pivot part 18 engaging same will be completely sealed within the interior of pivot part 18 thereby enhancing the anti-food and water retention properties of the joint.

The various features of the invention have been particularly shown and described, however, it should be obvious to one skilled in the art that modifications may be made therein without departing from the scope of the invention.

I claim:

1. A hinge product assembly for use in constructing hinged connections between artificial partial dentures and supporting natural teeth; said assembly comprising a bar, a pivot member and an attachment member; said bar being of generally rectangular cross-section having a cylindrical end surface having an axis at right angles to the longitudinal axis of said bar; said surface terminating in a shoulder extending across the bar parallel to the axis of said surface; said pivot member comprising a generally three sided hood shaped structure having interior surfaces closely conforming to the shape of said cylindrical end surface of said bar and loosely assembled thereto; the opposite end of said bar having securing means thereon and said attachment member surrounding said opposite end and in engagement with said means.

2. An assembly as claimed in claim 1 wherein said bar is constructed of permanent metal and said pivot and attachment members are constructed of wax whereby in constructing said connection said members are replaced by the fabricating metal used to form the connection.

3. An assembly as claimed in claim 1 wherein said bar is constructed of permanent metal and said pivot and attachment members are formed of plastic.

4. An assembly as claimed in claim 2 wherein said bar includes recessed bearing journals in either side thereof surrounding said axis of the cylindrical surface; whereby when said pivot member is replaced by metal, bearing pins will be formed closely engaging said journals.

5. A hinge assembly connecting an artificial partial denture support to a clasp device attached to a supporting natural tooth; said assembly comprising a bar, said clasp device including a pivot part and said support including an attachment part; said bar being of generally rectangular cross-section having a cylindrical end surface having an axis at right angles to the longitudinal axis of said bar; said surface terminating in a shoulder extending across the bar parallel to the axis of said surface; said pivot part comprising a generally three sided hood shaped structure having interior surfaces closely conforming to the shape of said cylindrical end surface of said bar and assembled thereto; the opposite end of said bar having securing notches therein and said attachment part surrounding said opposite end and in engagement with said notches.

6. An assembly as claimed in claim 5 wherein said bar includes recessed bearing journals in either side thereof surrounding said axis of the cylindrical surface and said pivot part including bearing pins closely engaging in said journals.

7. An assembly as claimed in claim 5 wherein said pivot part includes a stop surface engageable with said shoulder to limit pivotal movement of said bar with respect to said pivot part.

8. In a hinge product assembly for use in constructing a hinged connection between artificial partial dentures and supporting natural teeth, said assembly comprising an elongated bar, a heat destructible pivot member pattern and a heat destructible attachment member pattern, the attachment member being affixed by securing means to the one end of said bar member, the improvement comprising having said bar made of metal with a noncircular traverse cross section and having one end formed into a cylindrical surface having a cylindrical central axis at right angles to the longitudinal axis of said bar, opposite side walls of said one end being flat and at a right angle to the cylindrical axis, and including means for forming a bearing journal; said pivot member including a portion conformingly shaped to the cylindrical surface of said one end and also including sidewall portions formed as a unit with the cylinder surface conforming portion, which sidewall portions conform to the flat sidewalls of said one end of said bar and which sidewall portions aid in the forming of said bearing journal, so that said pivot member covers said one end of said bar in a hood-like manner and meets said bar in a close fit, without gaps, and said assembled bar and pivot member presents a smooth bottom surface.

9. The invention of claim 8 wherein a raised stop portion is provided on said cylindrical surface of said bar member, and said pivot member conforms thereto.

* * * * *